(12) United States Patent
Gianchandani et al.

(10) Patent No.: US 7,922,667 B2
(45) Date of Patent: Apr. 12, 2011

(54) ELECTROMAGNETIC FLOW SENSOR DEVICE

(75) Inventors: Yogesh B. Gianchandani, Ann Arbor, MI (US); Kenichi Takahata, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 1410 days.

(21) Appl. No.: 11/146,193

(22) Filed: Jun. 6, 2005

(65) Prior Publication Data
US 2005/0273014 A1    Dec. 8, 2005

Related U.S. Application Data

(60) Provisional application No. 60/576,956, filed on Jun. 4, 2004.

(51) Int. Cl.
*A61B 5/026* (2006.01)
(52) U.S. Cl. ........................................ 600/505; 600/454
(58) Field of Classification Search .................. 600/454, 600/504, 505, 345, 300, 486, 309, 508; 73/861.95, 73/861.17, 861.06; 128/879; 623/1.15, 1.34, 623/1.18; 607/60, 2; 606/98
See application file for complete search history.

(56) References Cited

U.S. PATENT DOCUMENTS

| | | | | |
|---|---|---|---|---|
| 3,019,647 A | * | 2/1962 | Beard et al. | 73/861.95 |
| 3,751,980 A | * | 8/1973 | Fryer | 73/861.17 |
| 3,838,683 A | * | 10/1974 | Kolin | 600/505 |
| 3,999,443 A | * | 12/1976 | Appel et al. | 73/861.17 |
| 5,040,422 A | * | 8/1991 | Frankenberger et al. | 73/861.05 |
| 5,907,893 A | * | 6/1999 | Zadno-Azizi et al. | 29/6.1 |
| 5,967,986 A | * | 10/1999 | Cimochowski et al. | 600/454 |
| 6,015,387 A | | 1/2000 | Schwartz et al. | |
| 6,053,873 A | * | 4/2000 | Govari et al. | 600/505 |
| 6,214,037 B1 | * | 4/2001 | Mitchell et al. | 623/1.11 |
| 6,442,413 B1 | * | 8/2002 | Silver | 600/345 |
| 6,586,699 B1 | | 7/2003 | Gianchandani et al. | |
| 6,895,265 B2 | * | 5/2005 | Silver | 600/345 |
| 6,917,833 B2 | * | 7/2005 | Denker et al. | 607/60 |
| 6,926,670 B2 | * | 8/2005 | Rich et al. | 600/459 |

(Continued)

OTHER PUBLICATIONS

Yoon et al., "Fabrication of a Micro Electromagnetic Flow Sensor for Micro Flow Rate Measurement," *Smart Structures and Materials 2000: Smart Electronics and MEMS, Proceedings of SPIE*, vol. 3990, pp. 264-271 (2000).

(Continued)

*Primary Examiner* — Charles A. Marmor, II
(74) *Attorney, Agent, or Firm* — Marshall, Gerstein & Borun LLP (57) ABSTRACT

Disclosed herein is an electromagnetic flow sensor device for monitoring flow of fluid in a channel. The sensor device includes a first electrode to be disposed along the channel and in communication with the fluid, a second electrode to be disposed along the channel and in communication with the fluid, and a radially expandable frame to structurally support the first electrode and the second electrode while conforming to the channel to position the first electrode and the second electrode along the channel. The device may also include an antenna coupled to the first and second electrodes to wirelessly provide an indication of a voltage induced between the first and second electrodes. In some embodiments, the radially expandable frame includes an insulating link such that the first and second electrodes are not electrically connected via the radially expandable frame. The sensor device may also include a structure having an inductance coupled to the first and second electrodes to wirelessly provide an indication of the induced voltage.

6 Claims, 9 Drawing Sheets

U.S. PATENT DOCUMENTS

2002/0179573 A1    12/2002    Gianchandani et al.
2004/0149294 A1    8/2004    Gianchandani et al.
2005/0080346 A1    4/2005    Gianchandani et al.

OTHER PUBLICATIONS

Kolin, "Approaches to Blood-Flow Measurement by Means of Electromagnetic Catheter Flow Meters," *IEEE Transactions on Magnetics*, vol. MAG-6, No. 2, pp. 308-314 (1970).

Kolin, "An Electromagnetic Catheter Blood Flow Meter of Minimal Lateral Dimensions," *Proc. of the Nat. Acad. of Sciences of the U.S.A.*, vol. 66, No. 1, pp. 52-56 (1970).

Chu, et al., "A Micromachined Kelvin Probe for Surface Potential Measurements in Microfluidic Channels and Solid-State Applications," *IEEE International Conf. on Sensors and Activators*, pp. 384-387 (2003).

Takahata, et al., "Coronary Artery Stents Microfabricated from Planar Metal Foil: Design, Fabrication, and Mechanical Testing," *IEEE Sixteenth Annual International Conf. on Microelectromechanical Systems*, pp. 462-465 (2003).

Takahata et al., "Batch Mode Micro-Electro-Discharge Machining," *Journal of Microelectromechanical Systems*, vol. 11, No. 2, pp. 102-110 (2002).

International Search Report for PCT/US2005/19819, mailed Sep. 6, 2006.

Written Opinion of the International Search Authority for PCT/US2005/19819, mailed Sep. 6, 2006.

\* cited by examiner

ELECTROMAGNETIC FLOW SENSOR DEVICE

RELATED APPLICATIONS

This application claims the benefit of provisional application Ser. No. 60/576,956, which was filed on Jun. 4, 2004, and entitled "Electromagnetic Blood Flow Sensor," the disclosure of which is hereby incorporated by reference.

STATEMENT REGARDING FEDERALLY SPONSORED RESEARCH OR DEVELOPMENT

The present invention was made in part with government support under Award No. ECS-0233174 from the National Science Foundation. The government has certain rights in the invention.

BACKGROUND OF THE DISCLOSURE

1. Field of the Disclosure

The present disclosure relates generally to flow sensors and, more particularly, to intraluminal electromagnetic flow sensors for fluids such as blood.

2. Brief Description of Related Technology

Chronic measurement of fluid flow is useful for long-term monitoring of many diseases, including those related to the heart, kidney, bile duct, etc. In coronary artery disease, constrictions of blood vessels are commonly treated by a medical procedure called balloon angioplasty with stent implantation. However, re-closures often occur due to recoil of the blood vessels or further plaque deposition. Monitoring the blood flow can provide advance notice of such failures. Detection mechanisms proposed in the past for implantable sensors include thermal resistor, blood conductance, differential pressure, and acoustic methods.

Blood flow has also been measured using electromagnetic flow sensors, which have two electrodes across which a voltage proportional to the fluid velocity is induced in accordance with Faraday's Law. As conductive fluid passes through an applied magnetic field, the electromotive force is generated and detected by the two electrodes.

An electromagnetic hood flow sensor disclosed in Kolin, "An Electromagnetic Catheter Blood Flow Meter of Minimal Lateral Dimensions," Proceedings of the National Academy of Sciences, Vol. 66, No. 1, pp. 53-56 (1970), utilized a catheter to place the two electrodes in the blood vessel. However, the catheter remains inserted throughout the measurement, rendering chronic, continuous, or long-term monitoring impracticable, if not impossible. Moreover, because the catheter remains inserted, the catheter and other aspects of the device must be small in size to, among other things, avoid inhibiting the blood flow. The small size of the device may then lead to insufficient flow sensitivity.

The principle of electromagnetic flow measurement has been demonstrated in connection with micro-sensors outside of the context of blood flow monitoring. For instance, in H. J. Yoon, S. Y. Kim, S. W. Lee, S. S. Yang, "Fabrication of a Micro Electromagnetic Flow Sensor for Micro Flow Rate Measurement," SPIE Symp. Smart Struc. Mat., pp. 264-71 (2000), a sensor is disclosed that has a pair of silicon substrates having respective opposing faces that meet to form a flow channel. Despite the small size of the two substrates and the sensor as a whole, the deployment and use of the sensor in connection with a blood vessel may be complicated by the defined nature of the flow channel.

SUMMARY OF THE DISCLOSURE

In accordance with one aspect of the disclosure, an electromagnetic flow sensor device is useful for monitoring flow of fluid in a channel. The device includes first and second electrodes to be disposed along the channel and in communication with the fluid, and a radially expandable frame to structurally support the first electrode and the second electrode while conforming to the channel to position the first electrode and the second electrode along the channel.

In some cases, the fluid includes blood and the channel includes a blood vessel. The sensor device may further include a helical structure to be disposed in the blood vessel and having an inductance coupled to the first and second electrodes to wirelessly provide an indication of a voltage induced between the first and second electrodes. The helical structure may provide scaffolding support to the blood vessel as a stent. The sensor device may still further include a voltage-controlled capacitor coupled to the inductance to form an LC tank.

In some embodiments, the radially expandable frame includes at least one insulative portion such that the first electrode and the second electrode are not electrically connected via the radially expandable frame. Alternatively, or in addition, the radially expandable frame includes first and second meander bands having the first and second electrodes disposed therein, respectively. The first and second meander bands may then be structurally coupled by an insulating link.

In accordance with one embodiment, the radially expandable frame includes a C-shaped structure circumferentially disposed along the channel. Alternatively, or in addition, the radially expandable frame is disposed within the channel. The radially expandable frame may alternatively include a circular ring disposed along an interior wall of the channel.

In some embodiments, the first and second electrodes include first and second conductive plates, respectively, and the radially expandable frame includes a first pair of serpentine beams and a second pair of serpentine beams. In these cases, the first conductive plate and the first pair of serpentine beams may form a first continuous conductive structure, and the second conductive plate and the second pair of serpentine beams may form a second continuous conductive structure. The first and second pairs of serpentine beams may plastically deform to position the first and second plates along an interior wall of the channel.

In accordance with another aspect of the disclosure, a device for monitoring blood flow in a blood vessel includes a radially expandable structure and an antenna. The radially expandable structure has a pair of electrodes and is disposed within the blood vessel to position the pair of electrodes in the blood vessel for an electromagnetic measurement of the blood flow via a voltage induced across the pair of electrodes. The antenna is coupled to the pair of electrodes to wirelessly provide an indication of the induced voltage.

In some embodiments, the radially expandable structure includes a ring disposed along an interior wall of the blood vessel. The antenna may also be disposed in the blood vessel. In addition, the antenna may include a stent having an inductance coupled to the pair of electrodes.

The radially expandable structure may include a plurality of serpentine frame portions that are plastically deformable to expand such that the radially expandable structure conforms to an interior wall of the blood vessel. Each serpentine frame portion of the plurality of serpentine frame portions may be of unitary construction with one of the pair of electrodes. The plurality of serpentine frame portions may include a conductive material, and the radially expandable structure may include at least one insulating link such that the pair of electrodes are not electrically connected via the plurality of serpentine frame portions.

In accordance with yet another aspect of the disclosure, a blood flow sensor for monitoring blood flow in a blood vessel includes a pair of electrodes, and a pair of bands to structurally support the pair of electrodes where each band is extendible to position the pair of electrodes along the blood vessel. The blood flow sensor further includes an insulating link to couple the pair of bands such that the pair of electrodes are not electrically connected via the pair of bands.

In some cases, each band includes a unitary structure microfabricated from planar steel foil. The blood flow sensor may also include a further insulating link coupling the pair of unitary structures such that the blood flow sensor forms a ring-shaped frame that conforms to the blood vessel when implanted.

In accordance with another aspect of the disclosure, a device for monitoring blood flow in a blood vessel includes a pair of electrodes to be disposed in the blood vessel for an electromagnetic measurement of the blood flow via a voltage induced across the pair of electrodes by the blood flow, and a structure to be disposed in the blood vessel and having an inductance coupled to the pair of electrodes to wirelessly provide an indication of the induced voltage.

In some embodiments, the structure provides support for the blood vessel as a stent. The device may further includes a voltage-controlled capacitance. Alternatively, or in addition, the device further includes a radially expandable frame to structurally support the pair of electrodes while conforming to the blood vessel to position the first electrode and the second electrode along the blood vessel. The radially expandable frame may include at least one insulative portion such that the pair of electrodes are not electrically connected via the radially expandable frame. The radially expandable frame may include a circular ring disposed along an interior wall of the blood vessel.

BRIEF DESCRIPTION OF THE DRAWING FIGURES

For a more complete understanding of the disclosure, reference should be made to the following detailed description and accompanying drawing figures, in which like reference numerals identify like elements in the figures, and in which.

While the disclosed flow sensor device is susceptible of embodiments in various forms, there are illustrated in the drawing (and will hereafter be described) specific embodiments of the invention, with the understanding that the disclosure is intended to be illustrative, and is not intended to limit the invention to the specific embodiments described and illustrated herein.

DETAILED DESCRIPTION OF PREFERRED EMBODIMENTS

Disclosed herein are flow sensors or flow sensing devices that have a structure suitable for electromagnetic transduction of fluid velocity in a channel, such as an intravascular blood flow. The electromagnetic transduction is implemented using two electrodes supported by, or integrated within, the structure (or frame), such that the electrodes may be disposed along the channel, arterial vessel, or other lumen through which the fluid flows. To this end, the structure may conform to an interior wall of the channel, arterial vessel, or other lumen once deployed, while residing in a different shape (e.g., planar) prior to deployment for ease in fabrication and/or deployment. In some embodiments, the structure includes a ring-shaped, intraluminal stainless steel cuff that integrally includes two electrodes in contact with the fluid flow. In the presence of a magnetic field, the fluid flow produces a voltage proportional to the fluid velocity across the two electrodes. As described herein, the structure may be fabricated by microelectro discharge machining and deployed by an angioplasty balloon.

In some embodiments, the structure may be coupled to, or integrated with, a stent device, which may be similarly fabricated and deployed. The stent device may provide structural support for the flow sensing device as well as scaffolding support to maintain the patency of the lumen. The stent may also provide communication functionality to facilitate the wireless transmission of flow data from the sensor site. In this and other ways, certain embodiments of the disclosed device utilize wireless communication techniques to support data transmission from the sensor site to an external receiver or other device.

Although well suited for, and described herein in connection with, the monitoring of blood flow in an arterial vessel, practice of the disclosed device is not limited to deployment in blood vessels or arterial monitoring applications. Rather, the disclosed sensor, sensing device, and sensor structure may be applied in any number of contexts or applications in which fluid flow within a channel is monitored. Possible contexts include, without limitation, a number of other non-arterial passages, such as respiratory passages, pancreatic ducts, lymphatic ducts, urinary tracts, biliary tracts, and the like. However, practice of the disclosed device is not limited to biomedical applications, but rather may be applied in non-biomedical contexts, such as fluid flow monitoring in applications where a lumen, other tubular structure, or channel may benefit from wireless monitoring via electrodes disposed therein. The disclosed device is particularly well suited for monitoring fluid flow when the sensor is to be inserted and disposed within a pre-existing flow path in a non-obstructive and non-disruptive manner, regardless of the nature of the fluid or purpose of the fluid path. Accordingly, the terms "intraluminal" and "lumen" are used herein without any implication that practice of the disclosed device is limited to a particular context or application. Furthermore, while the fluid flow sensors described herein are well suited for wireless monitoring of fluid flow, use of the devices and device structures disclosed herein is not limited to applications requiring or involving wireless communications.

The electromagnetic fluid flow sensing devices and device structures disclosed herein may be applied in the context of measuring or monitoring the velocity of any electrically conductive fluid, such as blood. The electromagnetic detection technique theoretically utilizes a device or system configuration in which the fluid flow, applied magnetic field, and the electrical sense axis are all perpendicularly arranged, although such exact arrangement is not a prerequisite for practice of the disclosed device. Nonetheless, this theoretical configuration yields a maximum induced voltage between the sensor electrodes in accordance with the equation:

$$V_{EM} = D \cdot B \cdot v,$$

where D is the diameter of the flow channel, B is the magnetic flux density of a uniform applied magnetic field, and v is the cross-sectional average velocity of an axially symmetric fluid flow. However, use of the disclosed device and device structures is neither limited to a system configuration that gives rise to the maximum induced voltage, nor limited to practice under the ideal conditions noted above. It should also be noted that the induced voltage is largely independent of fluid conductivity over a wide range, such that a number of different fluids may be suitably monitored. In the specific example of blood flow monitoring in an arterial vessel, the velocity profile is typically sufficiently axially symmetric, including at sites downstream from a narrowed portion of the vessel when the sensor site location is reasonably away from the blockage. Use of the disclosed devices and device structures may nevertheless be applied in such non-ideal situations through data processing or other adjustments directed to, for instance, monitoring relative changes in the fluid flow rather than the determination of absolute flow measurements.

As described further below, the disclosed structure may be machined from planar steel foil by batch-compatible micro-electro-discharge machining (micro-EDM). See, for example, Takahata et al., "Coronary Artery Stents Microfabricated From Planar Metal Foil: Design, Fabrication, and Mechanical Testing," IEEE Conf. MEMS, pp. 462-465 (2003), the teachings and disclosure of which are hereby incorporated by reference. The planar structures may then be plastically reshaped into a tubular shape by standard balloon angioplasty procedures. Alternatively, the structure may be fabricated from other structures, such as tubular foil, using other techniques, such as conventional laser machining techniques well known to those skilled in the art. Suitable micro-EDM fabrication process techniques are also described in detail in co-pending and commonly assigned U.S. patent application Ser. Nos. 10/737,314, and 10/079,312, entitled "Assembly And Planar Structure For Use Therein Which Is Expandable Into A 3-D Structure Such As A Stent And Device For Making The Planar Structure," and "Micro-Electro-Discharge Machining Method and Apparatus," respectively, as well as U.S. Pat. No. 6,586,699, entitled "Micro-Electro-Discharge Machining Utilizing Semiconductor Electrodes," the disclosures of which are also hereby incorporated by reference.

The disclosed structure, however, is compatible with a number of fabrication processes, materials, and designs. For instance, the fabrication of the disclosed device may utilize other micromachining fabrication processes, such as laser-based machining techniques. Such laser-based techniques may be relied upon in embodiments where the structure is formed from a pre-existing scaffolding or stent structure, such as one manufactured from tubular stainless steel.

The micro-EDM fabrication process described in the above-referenced materials advantageously relies upon planar metal foil or sheets as a starting material, but other materials and other shapes (e.g., tubular metal sheets) may be used to fabricate the disclosed device. In these embodiments, the structural material of the structure, e.g., stainless steel, also provides the electrical connections necessary for operation. However, in alternative embodiments, electrical traces may be disposed on a different material, such as a dielectric, used as a non-conductive structural support. In such cases, the shapes of the electrodes (and any other electrically functional components) are not as limited to the shape of the structural support or frame.

Figure 1:
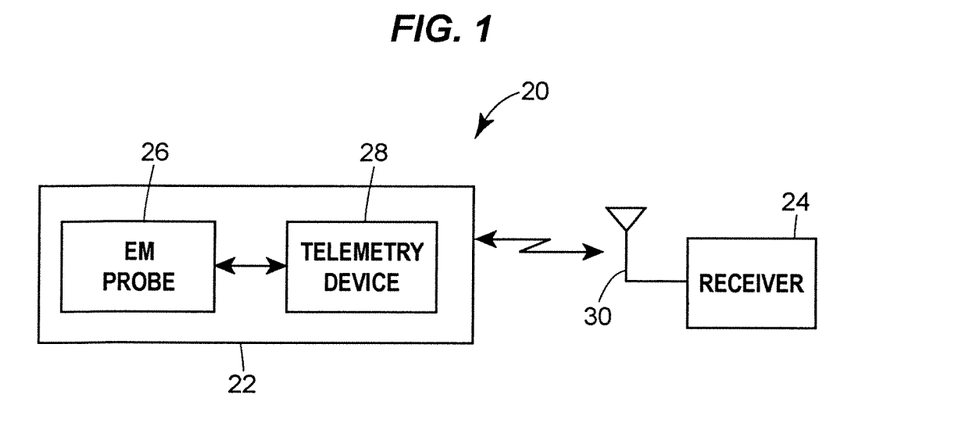
FIG. 1 is a block diagram of a flow sensor device in accordance with one aspect of the disclosure.

With reference now to FIG. 1, an electromagnetic blood flow sensor device or system indicated generally at 20 includes an implanted component 22 and an external receiver 24. The implanted component 22 includes an electromagnetic flow sensor or probe 26 coupled to a telemetry device 28, which supports communications with the receiver 24 via an antenna 30 associated or integrated therewith. In some embodiments, the telemetry device 28 includes a microchip that resides outside of the blood vessel, in which case circuitry is provided for both active signal readout and telemetry. As described below, the sensor device 20 need not rely on such active circuitry for communication.

The implanted component 22 may be partially or entirely intraluminal (e.g., intravascular). The degree to which the component 22 may be disposed within the blood vessel ranges from only having electrodes of the probe 26 in communication with the blood flow to having the entire implanted component 22 disposed within the blood vessel.

Figure 2A:
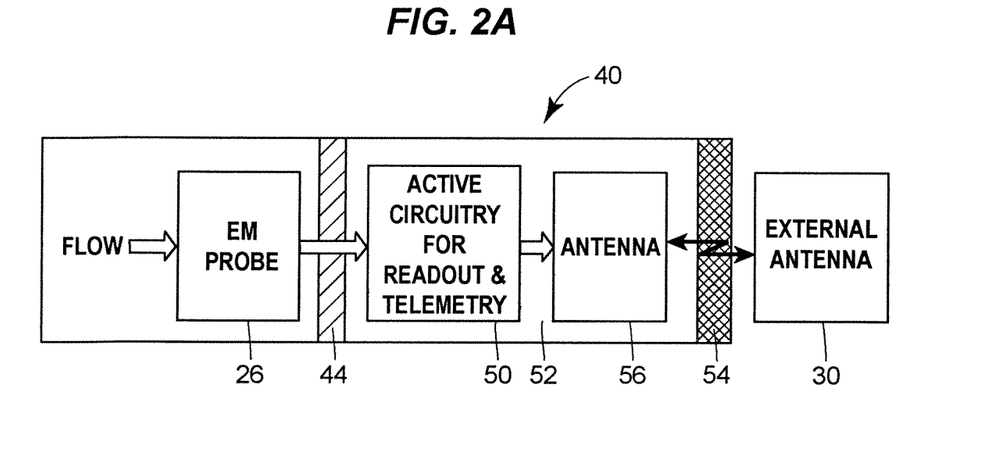
FIG. 2A is a schematic diagram of the flow sensor device of FIG. 1 in accordance with an active telemetry embodiment.
Figure 2B:
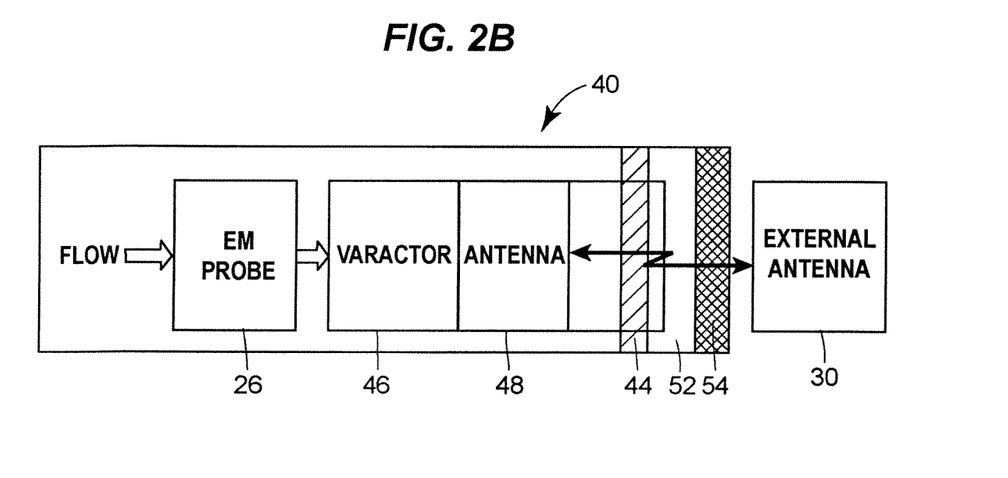
FIG. 2B is a schematic diagram of the flow sensor device of FIG. 1 in accordance with a passive telemetry embodiment.

FIGS. 2A and 2B schematically depict how two embodiments of the flow sensor device 20 may vary in the extent to which the implanted component 22 is intraluminal. The intraluminal aspects of the device 20 may also generally vary in accordance with whether an active or passive telemetry scheme is utilized in the delivery of blood flow information. Specifically, as shown in FIGS. 2A and 2B, electromagnetic blood flow sensor devices indicated generally at 40 and 42, respectively, include the intraluminal probe 26 (or at least electrode portions thereof, as described below) in communication with the blood flow. To this end, the probe 26 includes two electrodes insulated from each other and located diametrically across the blood vessel, as will be described further below.

FIGS. 2A and 2B schematically depict the intraluminal boundary as a blood vessel wall 44 having the blood flow and the probe 26 on one side thereof. As shown in FIG. 2B, the sensor device 42 includes intraluminal circuit elements and components in addition to the probe 26, such as telemetry-related components coupled to the probe 26. In this exemplary embodiment, a varactor 46 and an antenna stent 48 are coupled to the probe 26 to enable passive wireless communication with the receiver 24 via the antenna 30.

In the embodiment shown in FIG. 2A, the probe 26 passes blood flow information to a telemetry chip 50 that resides outside of the blood vessel wall 44. As described further below, the implanted component 22 (FIG. 1) may include wires passing through the blood vessel wall 44 to a nearby extravascular location 52 where the telemetry chip 50 is disposed beneath a skin layer 54. Also disposed at this extravascular location 52 is an antenna 56 coupled to (or integrated with) the telemetry chip 50 to support wireless transmission of data across the skin layer 54 to the antenna 30.

The embodiments shown in FIGS. 2A and 2B generally present alternative device architectures to support active and passive telemetry schemes, respectively. The active telemetry scheme may involve bypass surgery, insofar as the architecture involves accessing both the intraluminal environment as well as the extravascular location 52. In contrast, a passive telemetry scheme, for instance, that does not involve use of a large element, such as a battery, is compatible with standard angioplasty/stenting procedures and, therefore, may be considered less invasive. Practice of the disclosed device is therefore not limited to a particular deployment procedure. Moreover, the disclosed device is not limited to the embodiments shown in FIGS. 2A and 2B. Alternative embodiments may involve a hybrid or other combination of the embodiments, such as a case where both the antenna stent 48 and the implanted telemetry chip 50 are utilized to convey the blood flow information. More specifically, the antenna stent 48 may be relied upon as a passive telemetry component for communicating the blood flow information to the implanted telemetry chip 50, which could be small enough to be located intraluminally. The blood flow information may then be processed and transmitted to external devices, such as the receiver 24, as desired, with the added power and capabilities of the active telemetry provided by the telemetry chip 50. In this case, the telemetry device 28 (FIG. 1) includes both the passive circuit elements of the antenna stent 48 and the active circuitry for readout and telemetry of the telemetry chip 50.

Figure 3A:
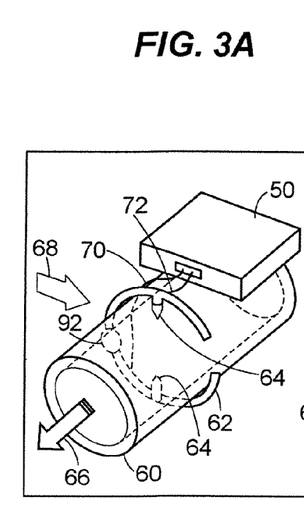
FIGS. 3A and 3B schematically depict the flow sensor device of FIG. 2A in greater detail and after deployment to monitor blood flow within a blood vessel.
Figure 3B:
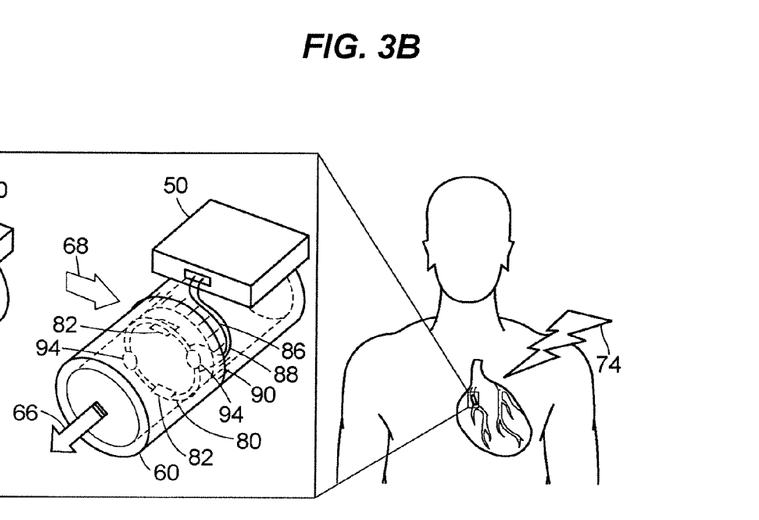

FIGS. 3A and 3B show two alternative configurations of the blood flow sensor device 40 of FIG. 2A after deployment to monitor blood flow within a blood vessel 60. In FIG. 3A, the blood flow sensor device 40 includes a micromachined, C-shaped cuff 62 wrapped around the blood vessel 60 and having penetrating electrodes 64. Blood flow 66 through the vessel 60 is monitored via the voltage induced between the electrodes 64 by the blood flow 66 in the presence of a magnetic field 68. An indication of the induced voltage is provided to the telemetry chip 50 via wires 70, 72 coupled to the electrodes 64. The telemetry chip 50 may include both voltage measurement and telemetry functionality to both process the signal carried via the wires 70, 72 and to generate one or more wireless signals 74 indicative of the blood flow information. Any one of a number of commercially available telemetry circuitry chips may be suitable for use with the blood flow sensor device 40 such that the wireless signals may be in accordance with a number of different, corresponding communication protocols (e.g., Bluetooth, Zigbee, etc.). In the future, further progress in the manufacturing technology of integrated circuits could shrink the size of the chip sufficiently to permit its location within the blood vessel As described herein, the functionality provided by the chip 50 may be implemented or integrated with other components of the device 40, such that telemetry, data transfer and other communications may be implemented in any suitable manner.

The embodiment shown in FIG. 3B includes a circular, micromachined, intraluminal cuff 80 to position two electrodes 82 inside the blood vessel 60. A C-shaped cuff similar to the one shown in FIG. 3A may be used in connection with this embodiment, but a circular shape may provide better support and stability for the electrodes 82. The voltage induced between the electrodes 82 is provided via wires 86, 88 that may pass through one or more suture sites 90 along the blood vessel 60.

The cuffs 62 and 80 of FIGS. 3A and 3B may include one or more insulating links to provide structural support while isolating the electrodes to allow the induced voltage to develop. Specifically, the C-shaped cuff 62 of FIG. 3A may include an insulating link 92, while the circular cuff 80 may include a pair of insulating links 94. Such insulating links may be useful in connection with embodiments having micromachined stainless steel as the primary structural component of the cuffs 62 and 80. In these cases, the electrodes 64 and 82 may be integrally formed with the cuffs 62 and 80 from the same stainless steel foil or other conductive film. As will be described further below, the processing of the stainless steel foil may include a gap-forming step to provide the electrode isolation, followed by the deposition of an insulating material to form the link.

Figure 3C:
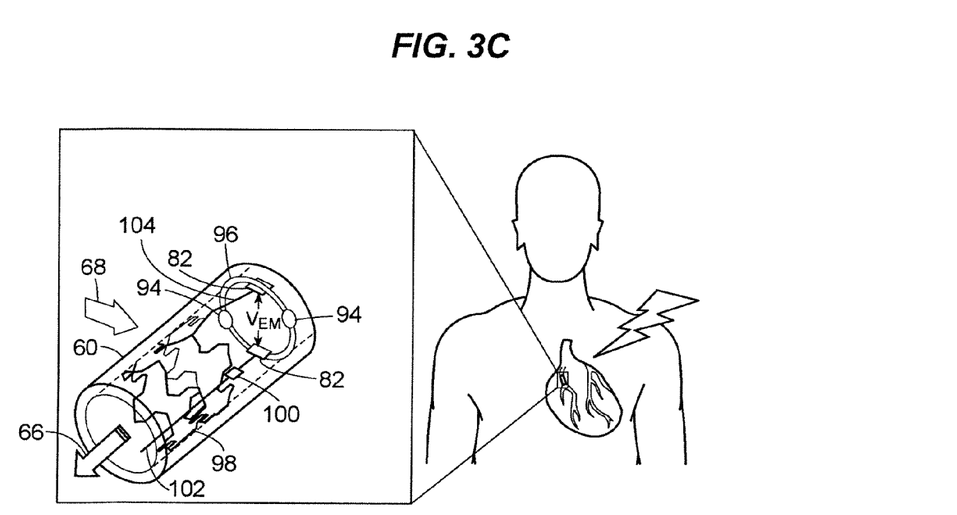
FIG. 3C schematically depicts the flow sensor of FIG. 2B in greater detail and after deployment to monitor blood flow within a blood vessel.

With reference now to FIG. 3C, the blood flow sensor 42 of FIG. 2B is shown after deployment and in accordance with an embodiment of the disclosed device utilizing a passive communication scheme. The blood flow sensor 42 may include a circular cuff 96, which may be similar in design, materials, construction and other aspects to the cuff 80 shown in FIG. 3B. Accordingly, the circular cuff 96 is shown with the electrodes 82 and the insulating links 94 common with that embodiment.

In this passive telemetry embodiment, the cuff 96 is coupled to a stent 98 having an inductive portion. The inductive portion may be helically shaped after deployment, further details of which are set forth below. The cuff 96 and the stent 98 may be both structurally and electrically coupled by a capacitive element 100 and longitudinal beams 102 and 104. More specifically, the electrodes 82 may be connected to the beams 102 and 104 to carry an indication of the voltage induced between the electrodes 82 to another portion of the device. To this end, the beams 102 and 104 may have a conductive portion, or be formed (e.g., micromachined) from stainless steel foil. The beams 102, 104, the stent 98, and the cuff 96 may therefore be integrally formed from the same stainless steel foil. But in cases where the beams 102, 104, the stent 98, and the cuff 96 are separately formed, the cuff 96 and the stent 98 may be formed from separate stainless steel foils.

As described below, the capacitive element 100 and the inductance presented by the stent 98 cooperate (and may be combined with further elements) to form an LC tank for delivering a wireless signal indicative of the voltage induced between the electrodes 82. In this embodiment, the LC tank is entirely made of passive, intraluminal circuit components, although in other embodiments the LC tank (or other elements involved in the telemetry) may include non-passive components, non-intraluminal components, or distributed or other non-circuit elements. Alternative embodiments utilizing a passive telemetry scheme need not include an LC tank having a characteristic modulated by the flow measurement. More generally, passive telemetry embodiments may modulate one or more characteristics of a signal indicative of the fluid velocity using any circuit having power delivered wirelessly thereto.

For instance, the blood flow sensor 42 shown in FIG. 2B may be modified to include an implanted telemetry or other IC chip, such as the telemetry chip 50, in wireless communication with the intraluminal LC tank. To this end, the telemetry chip 50 may include a planar coil (not shown) to interact with the inductive portion of the stent 98.

Figure 4:
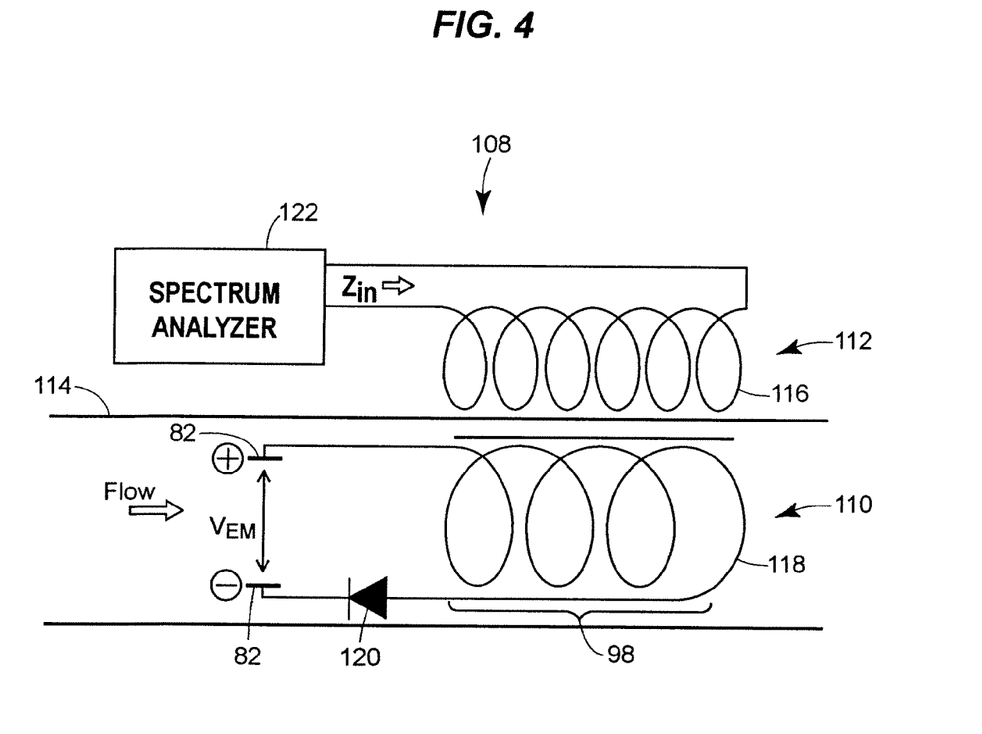
FIG. 4 is a schematic representation of the flow sensor of FIG. 2B in accordance with one embodiment.

A simplified, schematic representation of the passive telemetry scheme is shown in FIG. 4 in connection with an exemplary embodiment of a blood flow sensor device indicated generally at 108 and having an intraluminal component indicated generally at 110. The device 108 also includes a receiver indicated generally at 112 and disposed outside of a vessel wall 114 in either an implanted or non-implanted location. The receiver 112 includes an external coil 116 that acts as an antenna to generally collect the blood flow information carried by RF signals passively delivered or generated from, or influenced by, an internal coil 118 of the intraluminal component 110. More specifically, the internal coil 118 may be provided by the inductance of the stent device 98 (see also FIG. 3C), which is coupled to a capacitance to form an LC tank. In this exemplary embodiment, the capacitance is provided by the junction capacitance of a varactor diode 120, which is connected with the inductance in series. The ends of this series pair terminate in the two electrodes 82 (FIG. 3C) of the cuff 96, across which the voltage $V_{EM}$ is induced. In this way, the varactor diode 120 is biased by the voltage $V_{EM}$ to modulate the resonant frequency of the LC tank.

Because the turn-on voltage of the varactor diode 120 is much higher than the typical range of the voltage $V_{EM}$, the series-connected LC tank achieves a high input impedance to bias the varactor diode 120. More generally, the varactor diode 120 may, in alternative embodiments, be replaced by any varactor for which the change in capacitance would be maximized over the range of voltages generated by the targeted flow rates and for the available magnetic field per the equation indicated above. In any event, the varying capacitance in the LC tank results in a modification of the resonant frequency monitored via the input impedance Zin detected by a spectrum analyzer 122.

Alternative embodiments may involve one or more capacitances or other elements arranged to form any one of a number of LC tank configurations known to those skilled in the art. One may also use a circuit that is wirelessly powered (consistent with a passive scheme) to modulate the characteristics of the stent antenna or simply transmit data out.

Further details regarding the fabrication and design of the antenna stent 98, and its helical structure and inductive coil, may be found in co-pending and commonly assigned U.S. patent application Ser. Nos. 10/737,314 and 10/939,684, entitled "Assembly and planar structure for use therein which is expandable into a 3-D structure such as a stent and device for making the planar structure" and "Antenna stent device for wireless, intraluminal monitoring," respectively, the disclosures of which are hereby incorporated by reference.

Figure 5:
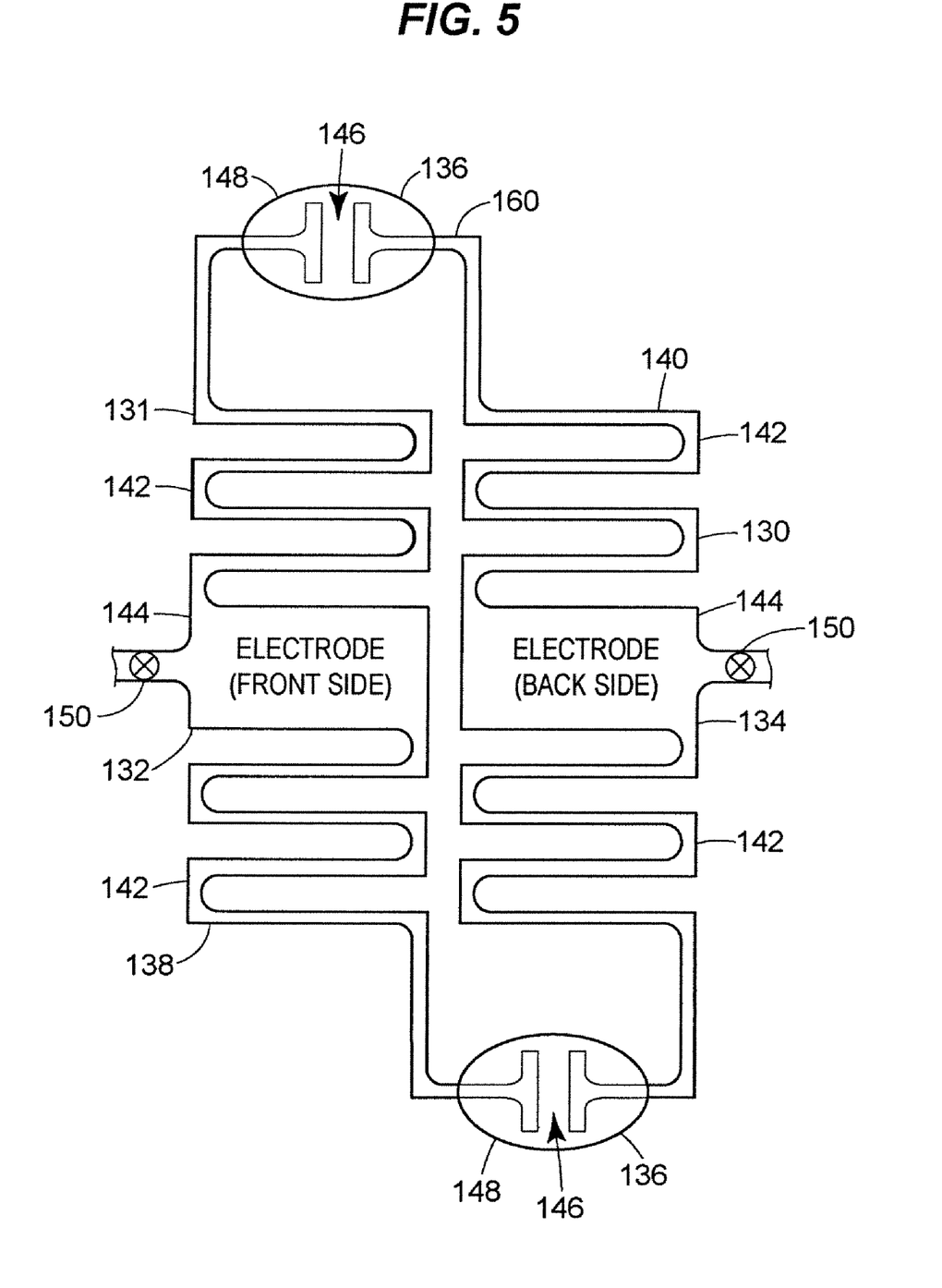
FIG. 5 is a plan view of a radially expandable structure of the flow sensor device in accordance with an embodiment shown in planar form prior to deployment.

With reference now to FIG. 5, the above-described probe 26 (FIGS. 2A, 2B), and the cuffs 62, 82 and 96 (FIGS. 3A, 3B, and 3C, respectively) may include a radially expandable structure 130 having a planar configuration or form prior to deployment. The exemplary embodiment shown in FIG. 5 has a pattern that forms a circular ring upon deployment and expansion through, for example, balloon angioplasty. To this end, the structure 130 generally includes a radially expandable frame 131 to support the electrodes of the sensor. In the embodiment of FIG. 5, the structure 130 includes a front side electrode 132 and a back side electrode 134. After expansion of the frame 131 and deployment of the structure 130 generally, the expanded configuration of the planar pattern shown in FIG. 5 conforms to the blood vessel to position both of the electrodes 132 and 134 along the blood vessel on inner walls thereof and in fluid communication with the blood (see, for example, FIGS. 8 and 9).

As shown in the exemplary embodiment of FIG. 5, the electrodes 132 and 134 are integrally formed with the remainder of the structure 130, which may correspond with the frame 131. Depending on the particular configuration, layout or materials used, the electrodes 132 and 134 may be considered part of, integrated with, or in unitary construction with, the frame portions of the structure 130.

The frame 131 includes one or more insulative portions or links 136 such that the electrodes 132 and 134 are not electrically connected via the radially expandable frame 131. The frame 131 further includes meander or involute bands 138 and 140 coupled via the links 136 and having the electrodes 132 and 134 disposed therein, respectively. On either side of the respective electrode 132, 134, each meander band 138, 140 may include a serpentine beam 142, which may but need not be identical to the one or more other serpentine beams of the frame 131. The serpentine beams 142 in each meander band 138, 140 are, in turn, coupled via a conductive plate 144 of the respective electrode 132, 134. At least a portion of each conductive plate 144 is in communication with the blood flow.

During deployment and expansion from the planar form, the serpentine beams 142 plastically deform to position the conductive plates 144 along the interior wall of the blood vessel. In alternative embodiments, the beams or other portions of the meander bands 138, 140 may have any shape that results in an extension of the meander band under radial expansion. Accordingly, the meander bands 138, 140 may have any number of U-shaped, V-shaped, or other bends of any desired angle that straighten for such extension, including or in addition to the serpentine bends shown in FIG. 5. Moreover, the bends may be rectilinear or curvilinear, or any combination thereof.

In certain embodiments, the conductive plates 144 and the serpentine beams 142 form a continuous conductive structure. For this reason, the insulating links 136 include a respective gap or other spacing indicated generally at 146 and about which is disposed a volume 148 of dielectric material, such as cement. The insulating links 136 mechanically tie the bands but electrically insulate them from each other, thereby allowing the induced voltage $V_{EM}$ to develop between the electrodes 132, 134.

In the exemplary embodiment shown in FIG. 5, the pair of meander bands 138,140 are composed of beams having a width of about 50 µm that wind back and forth with about 100 µm of separation. The beams eventually lead to the conductive plates 144, which may cover a rectilinear area of about 400 µm by 750 µm. The beams may, but need not, have the same width as the conductive plate 144 prior to extension, as is the case with the exemplary embodiment of FIG. 5. The gap 146 may present a spacing of about 100 µm.

The structure pattern may be machined using micro-EDM fabrication techniques on 50 µm-thick #304 stainless steel foil. After the insulating cement is applied and cured to fill and bridge the gaps 146, the structure 132 is released from the foil at release points 150. In some (e.g., non-wireless) embodiments, lead wires (not shown) may be bonded to the electrodes 132, 134 with conductive adhesive. All surfaces of the structure 132 except one side or portion of the conductive plates 144 of the electrodes 132, 134 may be coated with an insulating layer in the interest of avoiding spatial averaging which will reduce the voltage. Each electrode 132, 134 may optionally or additionally be coated with an anti-fouling layer. In one embodiment, two-part epoxy and enamel may be used for the cement and the insulation layer respectively.

FIGS. 6A-6D are schematic, plan views of a portion 160 (FIG. 5) of the radially expandable structure 130 in accordance with an exemplary embodiment fabricated via the above-referenced micro-EDM technique. The portion of the structure 130 shown may correspond with the meander band 138 near the insulating link 136. To further depict the structure 130 and the fabrication technique, FIGS. 6E-6H are cross-sectional views of the portion of the radially expandable structure 130 shown in FIGS. 6A-6D, respectively, taken along respective lines noted in FIGS. 6A-6D.

Figure 6A:
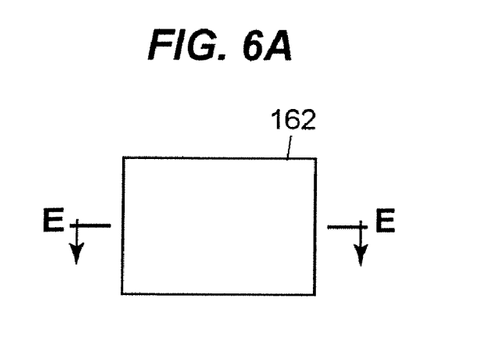
FIGS. 6A-6D are schematic representations of a portion of the radially expandable structure of FIG. 5 in accordance with an exemplary embodiment.
Figure 6B:
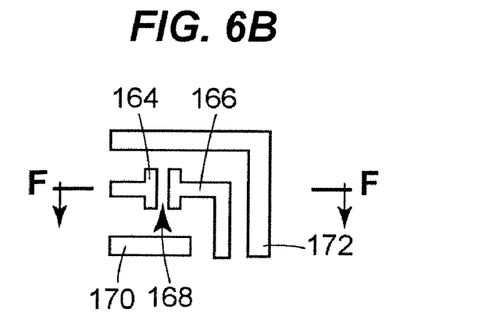
Figure 6C:
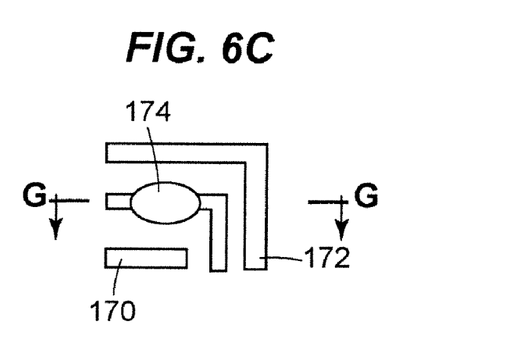
Figure 6D:
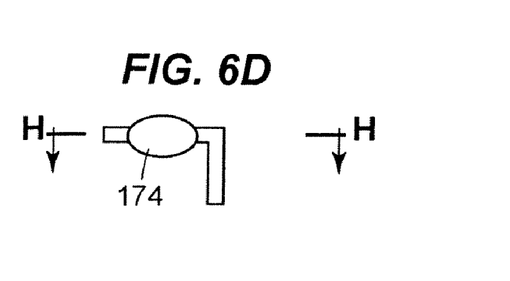
Figure 6E:
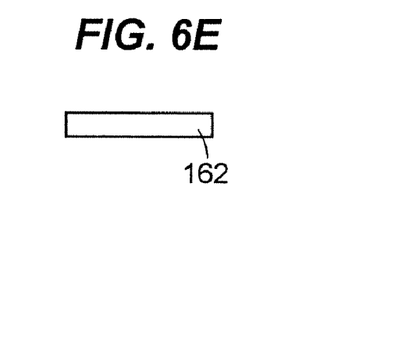
FIGS. 6E-6H are cross-sectional views of the portion of the radially expandable structure shown in FIGS. 6A-6D, respectively.
Figure 6F:
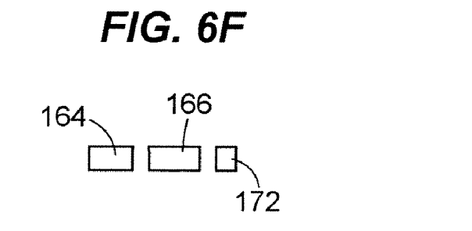
Figure 6G:
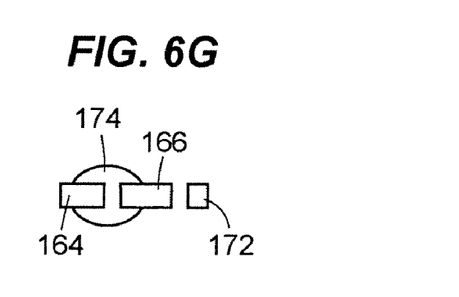
Figure 6H:
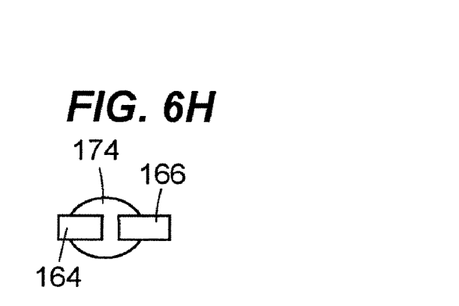

FIGS. 6A and 6B show the portion 160 of the structure 130 starting as part of a conductive film or foil 162, the size and shape of which are shown for convenience in illustration only. The conductive film 162 is machined into a pattern shown in FIGS. 6B and 6F, the pattern defining ends 164, 166 of the meander bands 138 that terminate at a gap indicated generally at 168. The pattern also includes temporary support portions 170, 172. FIGS. 6C and 6G then show the deposition of insulating cement 174 linking the ends 164, 166 and bridging the gap 168. Lastly, the structure 130 is released from the remaining portions of the foil, as shown in FIGS. 6D and 6H.

It should be noted that the structure 130 and the antenna stent 98 (FIG. 3C) may be fabricated from the same conductive film or foil. Moreover, in such cases, the structure 130 and the inductive coil of the antenna stent 98 may be integrally formed to be of unitary construction. Connecting beams coupling the structure 130 and the inductive coil may also be formed from the foil. Further information regarding the manner in which the structure 130 and the inductive coil may be coupled is described herein below in connection with the exemplary embodiments of FIGS. 8 and 9.

Figure 7:
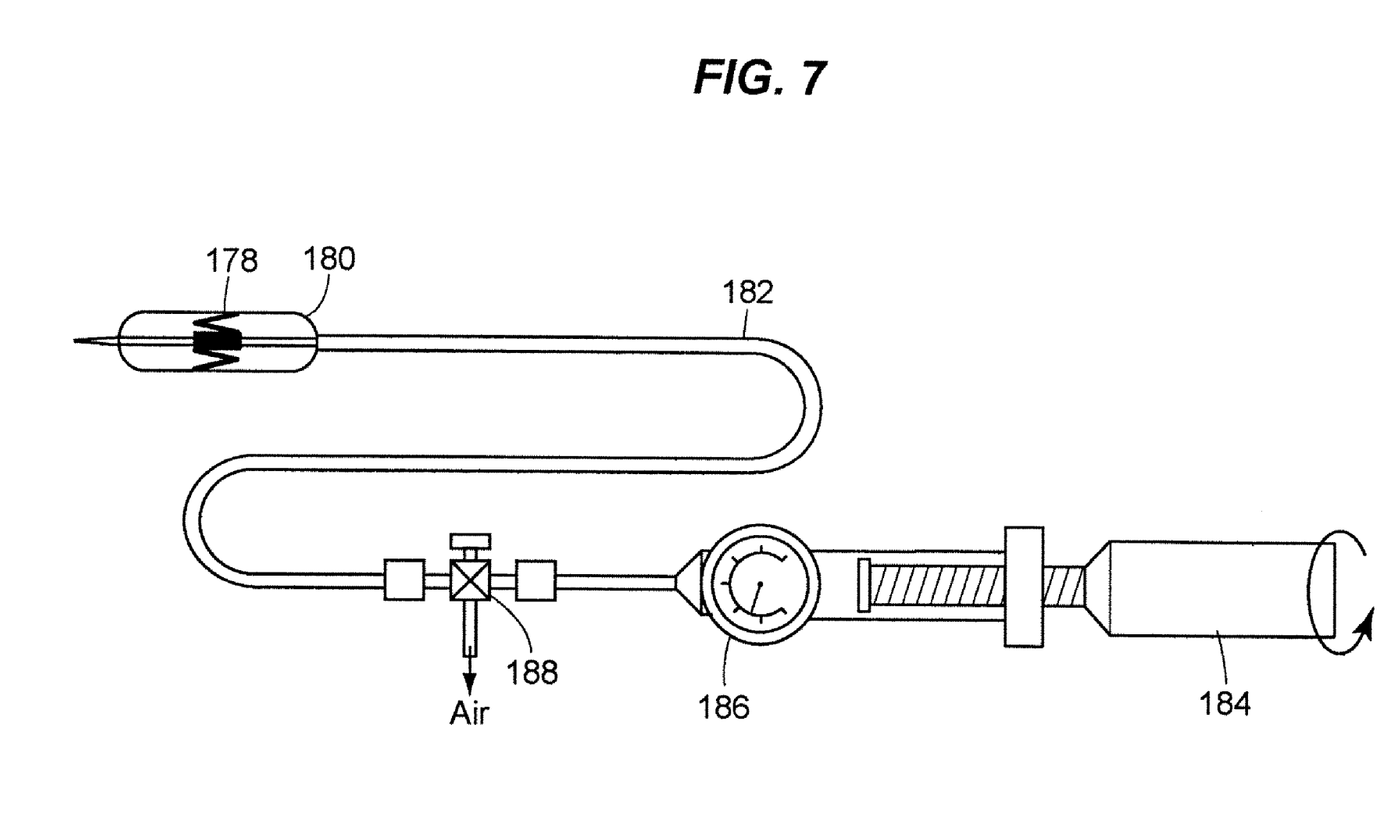
FIG. 7 is a schematic representation of an exemplary catheter-based deployment scheme for the flow sensor device of FIG. 5.

FIG. 7 is a schematic representation of an exemplary catheter-based deployment scheme for an exemplary flow sensor device 178, which may include the structure 130 (FIG. 5). The device 178 is mounted on a deflated balloon 180, which may be a portion of a standard angioplasty catheter 182, by threading the balloon 180 through the formerly planar structure 130 and other components of the device 178, such as the antenna stent 98. To this end, one of the meander bands 138 (FIG. 5) may be arched up, while the other meander band 140 is arched down. The relative directions are not material. In any case, the extension of the beams 142 allows the meander bands 138, 140 to form a ring through which the balloon 180 may slide. Upon inflation of the balloon 180 using, for instance, an inflation syringe 184, pressure gauge 186, and a vented three-way valve 188, one of the bands 138 is located above the balloon 180 whereas another band 140 is below the balloon 180. More generally, one band 138 is bent or arched in one direction, while the other band 140 is bent or arched in an opposite direction. As described above, the meander, serpentine, or zig-zag nature of each band 138, 140 permits such expansion without hinges or other mechanical formations.

The device 178 may then be deployed near a chronically or potentially diseased location in a blood vessel. In one example designed to approximate deployment in intravascular conditions, the device 178 was expanded inside a silicone tube with an internal diameter of 3-mm. The balloon 180 was inflated up to 7 atm. causing the lumen to expand to 3.5 mm in diameter. When the balloon was deflated and removed, the expanded cuff structure remained within the tube in position. Tests with flow velocities up to 2 m/s showed that both the structure and its placement were robust and immovable. It should be noted that maximum arterial flow is typically about 1.6 m/sec.

Figure 8:
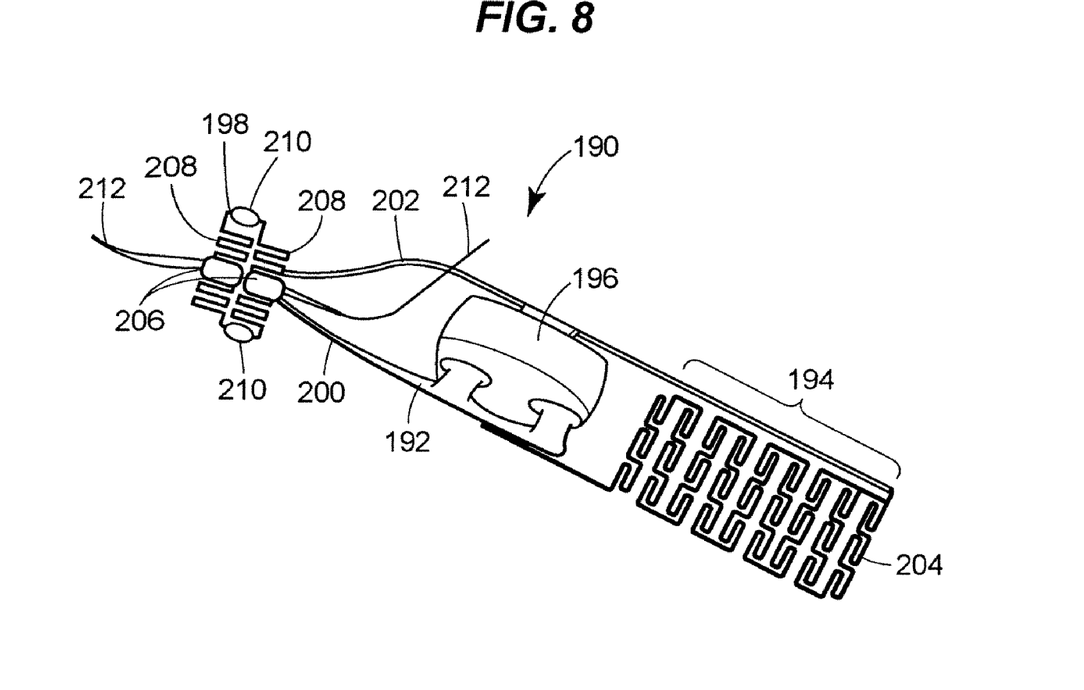
FIG. 8 is a photographic depiction of an exemplary flow sensor device with passive telemetry prior to deployment.

FIG. 8 shows an exemplary flow sensor device indicated generally at 190 prior to deployment. The device 190 utilizes a passive telemetry scheme and therefore has a structure 192 that includes an antenna stent 194 and a voltage-controlled capacitance or varactor 196 coupled to a sensor structure 198 via beams 200, 202. In this case, the antenna stent 194 includes a set of cross-bands 204 that will expand to form the helical portion. The sensor structure 198 includes a pair of electrodes 206, corresponding meander bands 208, and a pair of insulating links 210, to form the cuff as described herein above. The device 190 may also include a pair of leads 212 coupled to the electrodes 206 for testing or other purposes.

Figure 9:
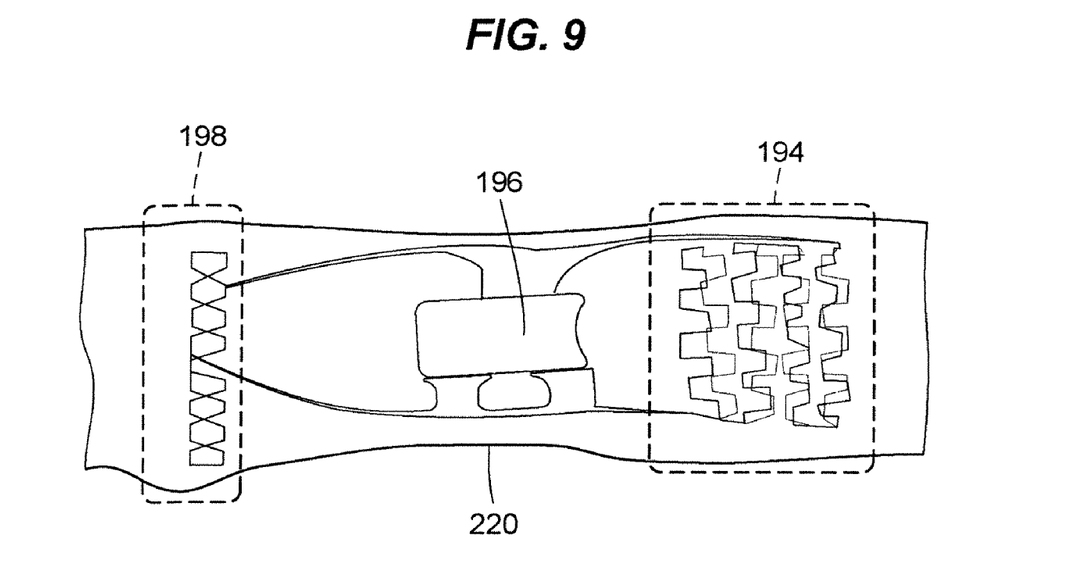
FIG. 9 is another photographic depiction of the exemplary flow sensor device of FIG. 8 after deployment in a silicone tube, or mock artery.

FIG. 9 shows the exemplary flow sensor device 190 of FIG. 8 after deployment in a silicone tube, or mock artery 220 (i.e., after the removal of the balloon). As shown, components of the structure 192 have radially expanded such that the antenna stent 194 and the sensor structure 198 are positioned along interior walls of the tube 220.

In the example shown in FIGS. 8 and 9, a commercially available diode was used as the varactor 196 (Fairchild Semiconductor Co., diode no. 1N3595). Planar structures of the cuff and the antenna stent were connected to the diode with a conductive adhesive. The antenna stent 194 was also fabricated by patterning a 50-µm thick stainless steel sheet with µEDM and then electroplated with Cu to reduce the parasitic resistance of the structure (i.e., increase quality factor of the tank). The resistance of the antenna stent 194, which was originally 14Ω, was reduced down to about $\frac{1}{10}$ of the value with 3-µm thick Cu coating. Another conductive material, such as gold, may be used instead of, or in addition to, copper. The planar structures were then coated with 1-µm thick parylene-C, which is a biocompatible polymer suitable for biomedical applications. The plates of the electrode 206 of the cuff were left uncoated. The diode was packaged with epoxy for both electrical and mechanical protection in this case. The device was deployed inside a 3-mm i.d. silicone mock artery with 0.25-mm wall thickness (Dynatek-Dalta, Inc., Mo.) by using the balloon catheter.

Figure 10:
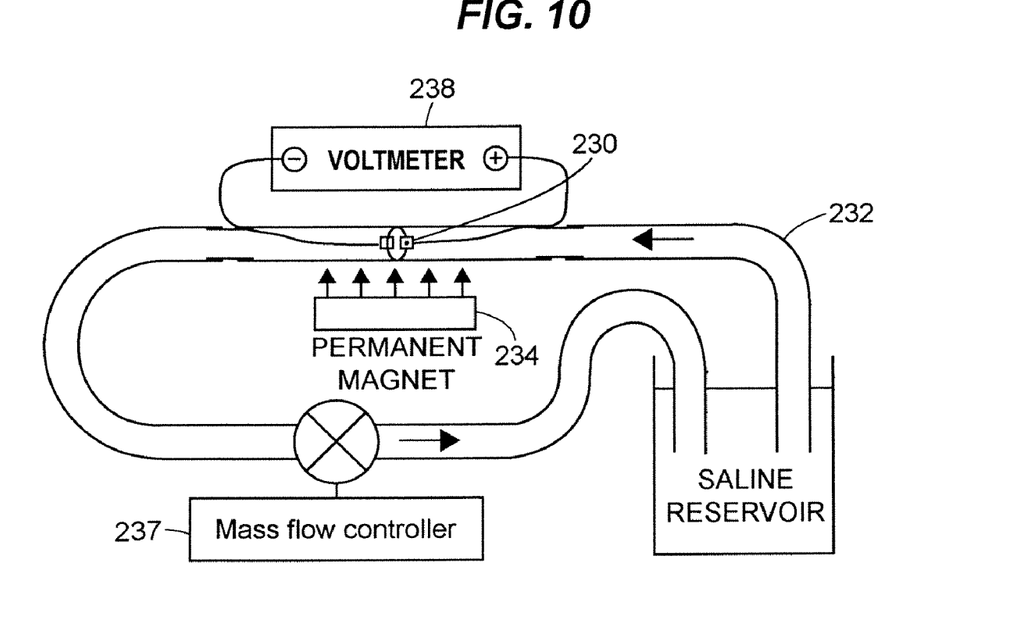
FIG. 10 is a schematic representation of a flow sensor device in an exemplary implementation in accordance with one aspect of the disclosure.

To test the performance of the cuff structure itself, an exemplary sensor device was implemented in accordance with an experimental test arrangement shown in FIG. 10. As described below, a device 230 having a stainless steel cuff was deployed inside a 3-mm internal diameter silicone tube 232 and demonstrated linear and symmetric responses of 3.1-4.3 micro-Volts per cm/sec over 180 cm/sec with fields of about 0.25 T created by a local permanent magnet 234 having a size of about 25×25×9 mm$^3$.

Figure 11:
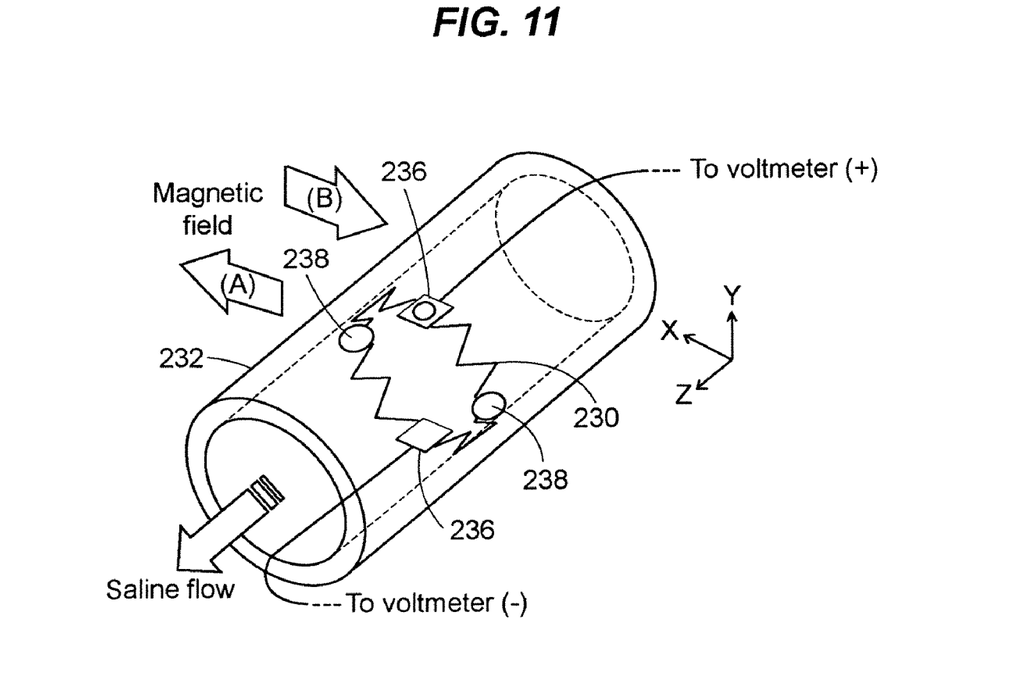
FIG. 11 is a partial, perspective view of the flow sensor device of FIG. 10 in greater detail.
Figure 12:
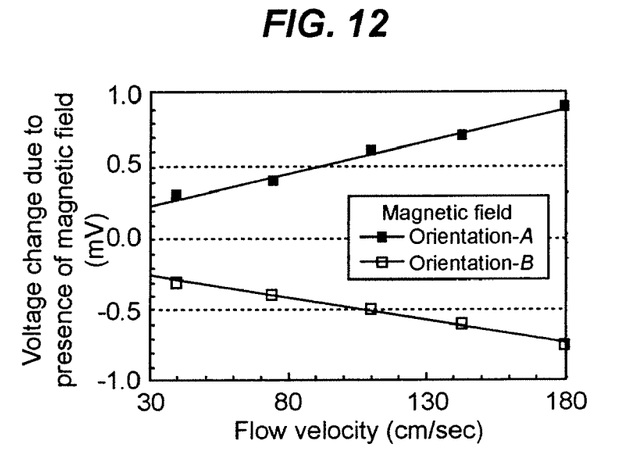
FIG. 12 is a plot depicting experimental measurement results from the exemplary implementation of the flow sensor device of FIG. 10 showing a linear dependence on fluid velocity and symmetric responses for opposing magnetic fields.

FIG. 11 shows the device 230 in greater detail. Electrodes 236 of the device 230 are positioned within the tube 232 using dielectric links 238, as described above, relative to two alternative orientations of the magnetic field. As depicted in FIG. 12, the output is shown to be linearly dependent in accordance with the orientation of electrodes and the magnetic field.

The cuff was expanded from a 50-micron thick planar microstructure having overall dimensions of 2.7×1.6 mm$^2$. The planar structure was then assembled on a deflated angioplasty balloon, and plastically expanded to ring shape by inflation of the balloon inside a silicone tube. The expanded cuff was lodged on inner walls of the tube 232 by its own pressure and remained immovable in at least 2-m/s flow. Fluidic tests that used saline and a DC magnetic field of 0.25 T demonstrated linear response of electromagnetically induced voltage to varied flow speed. The measurement results exhibited reasonable match to theoretical analysis. To circumvent polarization sensitivity and allow amplification of the output signal, an AC magnetic field may be used instead of the DC operation set forth in connection with this embodiment.

With reference again to FIG. 10, a pump/flow-controller 237 regulated the flow of 2% wt. saline and a voltmeter 238 measured the voltage between electrode leads connected to the electrodes 236. While the permanent magnet 234 was used to generate and provide the magnetic field in this example, any number of other magnetic field generators may be used. Permanent magnets provide one low-power solution, but those skilled in the art will appreciate the variety of magnetic field generators that may be integrated with the electromagnetic cuff sensor. The field orientation was perpendicular to both flow direction and the voltage sense axis defined by the locations of the two electrodes. The magnetic field was characterized by an InAs Hall sensor (F. W. Bell, FL, model BH-205) and measured to be about 0.25 T at the location of the cuff. The presence of the cuff had no detectable impact on the externally measured magnetic field. To determine the electromagnetic effect, voltage change due to varying flow rate was measured with opposing orientations of the magnetic field as shown in FIG. 10. The voltage change relative to a baseline value, which is associated with polarization and electrochemical effects, is plotted in FIG. 11. The voltage linearly and symmetrically increased or decreased depending on the orientation. The voltage response and sensitivity in this test were 3.1-4.3 microV per cm/sec and 50-70 ppm per cm/sec, respectively.

Figure 13:
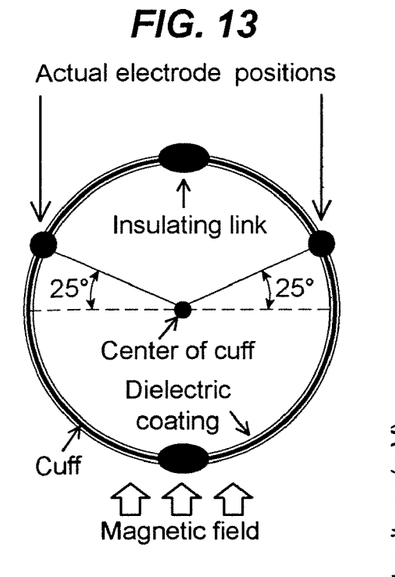
FIG. 13 is a schematic, cross-sectional representation of a flow sensor device having non-diametrical electrode positioning; and, FIG. 14 is a plot depicting a comparison of experimental measurement results from the exemplary implementation of the flow sensor device of FIG. 10 with theoretical results associated with three flow sensors having electrodes either diametrically aligned or misaligned to varying degrees.
Figure 14:
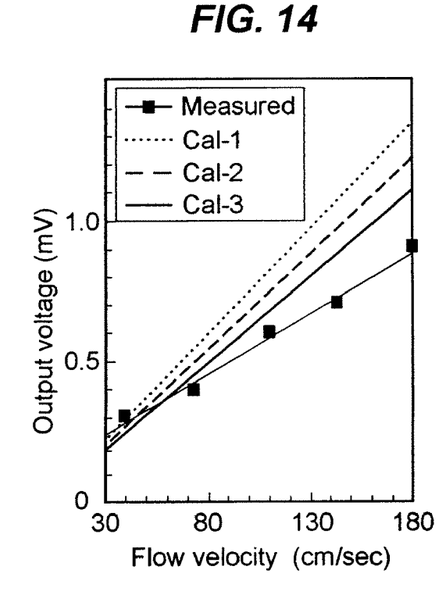

Using the standard equation for the induced voltage, with D=3 mm and B=0.25 T, the calculated output voltages are plotted with a dotted line (Cal-1) in FIG. 14. Although at lower flow velocity the prediction matches well with the experimental results (also plotted in FIG. 14 with square dots), it deviates as the flow velocity is increased. FIG. 13 shows actual electrode positions observed in the expanded cuff, where they are not actually on a diametrical line but are shifted by approximately 50 degrees in total during the balloon expansion. This non-uniform expansion can lower the output voltage. Two hypothetical cases are evaluated and plotted in FIG. 14: each of electrodes is equally offset by 25 degrees as shown in FIG. 13 (Cal-2), and one of electrodes is offset by the whole 50 degrees (Cal-3). The plots indicate that the latter case shows closer match to the measurement, although the deviation from the measured values is still not negligible. A potential cause for this mismatch is a loss associated with non-ideal profile of flow velocity. The presence of electric leads which are connected to the electrodes and/or the cuff itself can disturb the flow. The sensitivity to local flow velocity varies across the channel and rapidly increases close to the electrodes. Thus, the disturbance near an electrode due to the boundary irregularities can potentially require a correction factor to be introduced into the theoretical estimate, which is otherwise idealized. Lead wires that were attached directly to the electrodes and the use of relatively large electrodes (400×750 microns2) in the set-up may also contribute to the reduced response. However, the latter tends to reduce the sensitivity to the electrode position error because of the averaging effect.

Described herein above is an electromagnetic blood flow sensor which presents several operational advantages over, for instance, those based on pressure sensing, including: a linear relationship between the output and flow; less output dependence on cross-sectional flow profile; and, elimination of the need for sensing diaphragms. Each of these advantages may result in improvements in both reliability and operational lifetime. In addition to improved and more robust operational characteristics, the disclosed flow sensor may have a cuff structure advantageously fabricated in batch fashion using micromachining techniques. The cuff structure may, but need not be, fabricated from planar stainless steel foil using batch-compatible micro-electro-discharge machining and subsequently plastically reshaped into a ring by inflating a cylindrical balloon inside a blood vessel. The cuff has a pair of electrodes which are separated from each other by one or more insulating links. A dielectric layer coats all surfaces except the electrodes.

The completed structure does not rely upon or use any bonded or hinged joints, and exhibits excellent mechanical strength. The balloon expansion technique is suitable for tailoring the final diameter of the cuff to the actual inner diameter of an artery at the location of the implant. The micro-EDM fabrication process is also useful for the cuff because it provides a planar approach to the micromachining of stainless steel, which is a suitable structural material. The electrical isolation of different parts of the structure is then provided via insulating segments.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding only, and no unnecessary limitations should be understood therefrom, as modifications within the scope of the invention may be apparent to those having ordinary skill in the art.

What is claimed is:

1. A device for monitoring blood flow in a blood vessel, the device comprising:
   a pair of electrodes to be disposed in the blood vessel such that each electrode is in communication with the blood flow to electromagnetically measure the blood flow via a voltage induced across the pair of electrodes by the blood flow; and,
   a structure to be disposed in the blood vessel and having an inductance directly coupled to the pair of electrodes to wirelessly provide an indication of the induced voltage, wherein the structure and the pair of electrodes combine to form a passive assembly to passively provide the indication of the induced voltage to an external receiver inductively coupled to the structure, wherein the structure and the pair of electrodes have a planar configuration when in a non-deployed position.

2. The device of claim 1, wherein the structure provides support for the blood vessel as a stent.

3. The device of claim 1, further comprising a voltage-controlled capacitance.

4. The device of claim 1, further comprising a radially expandable frame to structurally support the pair of electrodes while conforming to the blood vessel to position the first electrode and the second electrode along the blood vessel.

5. The device of claim 4, wherein the radially expandable frame includes at least one insulative portion such that the pair of electrodes are not electrically connected via the radially expandable frame.

6. The device of claim 4, wherein the radially expandable frame comprises a circular ring disposed along an interior wall of the blood vessel.

* * * * *